(12) United States Patent
Wang et al.

(10) Patent No.: US 9,034,894 B2
(45) Date of Patent: May 19, 2015

(54) DERIVATE, PREPARATION METHOD AND USE OF 10-METHOXYCAMPTOTHECIN

(75) Inventors: Yang Wang, Heilongjiang (CN); Xiufeng Yan, Heilongjiang (CN); Lijia Jing, Heilongjiang (CN); Weimin Ding, Heilongjiang (CN); Jian Zheng, Heilongjiang (CN); Qiuying Pang, Heilongjiang (CN); Tao Yu, Heilongjiang (CN)

(73) Assignee: NORTHEAST FORESTRY UNIVERSITY, Heilongjiang (CN)

( * ) Notice: Subject to any disclaimer, the term of this patent is extended or adjusted under 35 U.S.C. 154(b) by 0 days.

(21) Appl. No.: 14/124,570

(22) PCT Filed: Jun. 15, 2012

(86) PCT No.: PCT/CN2012/076990
§ 371 (c)(1),
(2), (4) Date: Mar. 3, 2014

(87) PCT Pub. No.: WO2012/175002
PCT Pub. Date: Dec. 27, 2012

(65) Prior Publication Data
US 2014/0194458 A1 Jul. 10, 2014

(30) Foreign Application Priority Data
Jun. 23, 2011 (CN) .......................... 2011 1 0169681

(51) Int. Cl.
*C07D 491/22* (2006.01)
(52) U.S. Cl.
CPC .................................. *C07D 491/22* (2013.01)

(58) Field of Classification Search
None
See application file for complete search history.

(56) References Cited

U.S. PATENT DOCUMENTS 4,473,692 A * 9/1984 Miyasaka et al. ............... 546/48
4,545,880 A * 10/1985 Miyasaka et al. ........ 204/157.71

FOREIGN PATENT DOCUMENTS

WO          03095461       11/2003
WO         2006089207       8/2006

OTHER PUBLICATIONS

Adamovics et al., 18(6) Phytochemistry 1085-6 (1979) (CAS Abstract).*
Li, Shiyou et al., Induced endogenous autotoxicity in Camptotheca, Frontiers in Bioscience, Elite Edition, vol. E2, No. 4, pp. 1196-1210, ISSN: 1945-0508, see p. 1199, section 4.3, table 1, compounds 5 and 11.

* cited by examiner

*Primary Examiner* — Timothy R Rozof
(74) *Attorney, Agent, or Firm* — Vidas, Arrett & Steinkraus

(57) ABSTRACT

Provided is a 10-methoxycamptothecine derivate of formula (1), wherein R is selected from hydrogen, $C_{1-6}$ alkyl, $C_{1-6}$ haloalkyl, aryl substituted $C_{1-6}$ alkyl, phosphate substituted $C_{1-6}$ alkyl, amino-substituted $C_{1-6}$ alkyl, carboxyl substituted $C_{1-6}$ alkyl, hydroxyl substituted $C_{1-6}$ alkyl, and amide-substituted $C_{1-6}$ alkyl; $R_1$ is selected from hydrogen and t-butoxycarbonyl substituted amino. Also provided in the present invention are the preparation method of the derivate and the use thereof in anti-tumor drug preparation.

14 Claims, No Drawings

DERIVATE, PREPARATION METHOD AND USE OF 10-METHOXYCAMPTOTHECIN

CROSS-REFERENCE TO RELATED APPLICATIONS

This application claims the benefit of PCT Application No. PCT/CN2012/076990, filed Jun. 15, 2012, which claims priority to Chinese Patent Application No. 201110169681.0, filed Jun. 23, 2011, the entire content of each of which are hereby incorporated herein by reference.

FIELD OF THE INVENTION

This invention relates to the field of medicinal chemistry and therapeutics, in particular to new 10-methoxycamptothecin derivatives, preparation and use thereof.

BACKGROUND

Camptothecin (CPT) is an alkaloid extracted from Chinese endemic plant—Camptotheca acuminata—in 1966 by Wall et. al for the first time. In the early activity screening in vitro, camptothecin shows strong anti-tumor activity and significant inhibition against a variety of solid tumors and leukemia. However, camptothecin has poor water-solubility and strong adverse side-effects, thus it is limited for its application in cancer treatment. 10-Methoxycamptothecin is a natural derivative of camptothecin which has better anti-tumor activity than camptothecin, but also more toxic. In 1985, Hsiang Y. H. et. al found that camptothecin exhibits cytotoxic activity by inhibiting Topoisomerase I, which causes the people's attention to camptothecin again. Many researchers have begun to focus on modification and improvement to the chemical structure of camptothecin, and committed to improve its absorption in human body and enhance its therapeutic effects. So far, two kinds of camptothecin derivatives—Topotecan and Irinotecan—have been approved by the U.S. Food & Drug Administration (FDA) listed for the treatment of recurrent ovarian cancer and rectal/colon cancer. Another variety of derivatives such as 9-Nitrocamptothecin, 9-aminocamptothecin, CKD-602, DX-9815f, GI-147211 are also in various stages of clinical trials. The closed α-hydroxylactone ring in camptothecin structure is the essential structure for maintaining the anti-tumor activity thereof, but the α-hydroxylactone ring is easily hydrolyzed and open-looped in the human body to form a carboxylate structure, and the open-looped structure is easily bound to human serum protein so as to loss the anti-tumor activity.

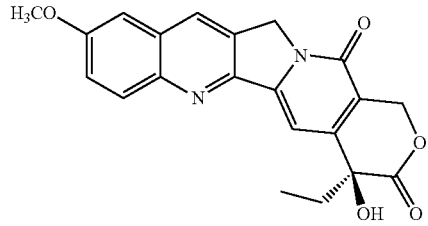 [SMILES: CC[C@@]1(O)C(=O)OCc2c1cc1n(c2=O)Cc2cc3cc(OC)ccc3nc2-1]

Chemical Formula of 10-methoxycamptothecin

BRIEF SUMMARY OF THE INVENTION

An object of the present invention is to provide new 10-methoxycamptothecin derivatives with high-efficiency and low toxicity.

Another object of the present invention is to provide a method for preparing the 10-methoxycamptothecin derivatives.

Another object of the present invention is to provide a use of the 10-methoxycamptothecin derivatives and compositions thereof as the anti-tumor drugs.

In order to achieve the above objects, the present invention is provided with 10-methoxycamptothecin derivatives having a general formula (1).

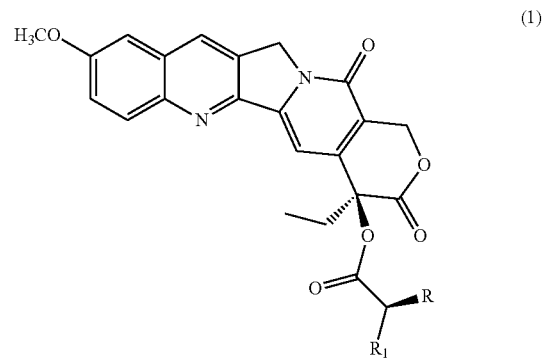

In formula (1), R represents a substituent group and is selected from hydrogen, $C_{1-6}$ alkyl, $C_{1-6}$ haloalkyl, aryl-substituted $C_{1-6}$ alkyl, phosphate-substituted $C_{1-6}$ alkyl, amino-substituted $C_{1-6}$ alkyl, carboxyl-substituted $C_{1-6}$ alkyl, hydroxyl-substituted $C_{1-6}$ alkyl, and amide-substituted $C_{1-6}$ alkyl; and $R_1$ represents a substituent group and is selected from hydrogen and t-butoxycarbonyl-amino.

In particular, R is selected from hydrogen. $C_{1-6}$ alkyl, aryl-substituted $C_{1-6}$ alkyl, and $R_1$ is selected from hydrogen and t-butoxycarbonyl-amino.

In formula (1), if $R_1$ is hydrogen, R is selected from:

—$CH_3$

In formula (1), if $R_1$ is t-butoxycarbonyl-amino, R is selected from:

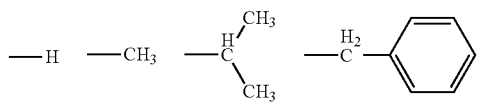

In particular, if $R_1$ is t-butoxycarbonyl-amino, R is selected from:

—$CH_3$

The present invention provides a method for preparing the 10-methoxycamptothecin derivatives, which comprises reacting 10-methoxycarnptothecin with N-t-butoxycarbonyl-amino acid or carboxylic acid by esterification under coupling agent and catalyst to form the 10-methoxycamptothecin derivatives of the formula (1).

In particular, the present invention provides a method for preparing the 10-rnethoxy-camptothecin derivatives, comprising the following steps;

1) Adding 10-methoxycamptothecin, coupling agent and catalyst into a solution of N-t-butoxycarbonyl-amino acid or carboxylic acid dissolved in organic solvent to effect an esterification reaction;

2) Filtering the esterification products, adding distilled water into the filtrate until precipitation to obtain a crude 10-methoxycamptothecin derivative.

Furthermore, the method also comprises step 3): effecting a purification process of the crude 10-methoxycamptothecin derivative.

Especially, the purification process comprises: filtering, water washing, drying and column chromatography separation of the precipitates successively to obtain the 10-methoxycamptothecin derivative.

The N-t-butoxycarbonyl-amino acid is selected from N-t-butoxycarbonyl-glycine, N-t-butoxycarbonyl-L-alanine, N-t-butoxycarbonyl-L-phenylalanine, or N-t-butoxycarbonyl-L-valine. The carboxylic acid is selected from propionic acid; and the organic solvent is selected from dimethyl sulfoxide or N,N-dimethyl formamide.

In particular, the coupling agent is selected from N,N'-dicyclohexylcarbodiimide (DCC), N,N'-Carbonyldiimidazole, (CDI) or 1-(3-dimethylamino-propyl)-3-ethylcarbodiimide hydrochloride (EDC.HCl). The catalyst is selected from pyridine and/or 4-Dimethylaminopyridine (DMAP).

The present invention also involves a number of drug compositions containing the 10-methoxycamptothecin derivatives of the present invention as active ingredients and pharmaceutically acceptable carriers.

The term "pharmaceutically acceptable carriers" herein refers to: one or more solid or liquid compatible fillers or gel materials, which are suitable for human to use and have adequate purity and low enough toxicity. "Compatibility" herein refers to that each component in the composition can blend with the compounds of the present invention and each other, but not significantly reducing the efficacy of the compounds. Some examples of the pharmaceutically acceptable carriers include carbohydrates (such as glucose, sucrose, lactose, etc.), starches (such as corn starch, potato starch, etc.), cellulose and its derivatives (such as sodium carboxymethyl cellulose, sodium ethyl cellulose, cellulose acetate, etc.), gelatin, talc, solid lubricants (such as stearic acid, magnesium stearate), calcium sulphate, vegetable oil (such as soybean oil, sesame oil, peanut oil, olive oil, etc.), polyols (e.g., propylene glycol, glycerin, mannitol, sorbitol, etc.), emulsifiers (e.g., Twains), lubricants (e.g., sodium dodecyl sulfate), colorants, flavoring agents, stabilizers, antioxidants, antiseptics, pyrogen-free water, and so on.

Dosage form of the drug compositions is selected from tablet, capsule, pill, injection, sustained-release preparation, controlled-release preparation, or various particulate drug-delivery systems.

The invention also relates to the use of the 10-methoxycamptothecin derivatives of the present invention in preparation of anti-tumor drugs.

The in vitro activity screening experiments showed that the 10-methoxycamptothecin derivatives with the general formula (1) have significant anti-tumor effects and good dose-response relationship. The half inhibitory concentration ($IC_{50}$) of the 10-methoxy-camptothecin derivatives had been determined by using ovarian cancer cell line 2774 as the tested cell lines in the thiazole blue colorimetric method, wherein the $IC_{50}$ of 10-methoxycamptothecin-20-O—(N'-t-butoxycarbonylglycine ester is 355.9±43.38 mmol/ml, the $IC_{50}$ of 10-methoxycamptothecin-20-O—(N'-t-butoxycarbonyl)-L-alanine ester is 46.73±21.74 nmol/ml, the $IC_{50}$ of 10-methoxycamptothecin-20-O—(N'-t-butoxycarbonyl)-L-phenylalanine ester is 393.56±21.74 nmol/ml, the $IC_{50}$ of 10-methoxycamptothecin-20-O—(N'-t-butoxycarbonyl)-L-valine ester is 1971.30±93.59 nmol/ml, and the $IC_{50}$ of 10-methoxycamptothecin-20-O-propionate is 841.53±50.11 nmol/ml.

DESCRIPTION OF THE PREFERRED EMBODIMENTS

The present invention will be further described in details by the following examples. The following examples mainly describe the embodiments of the present invention, but the present invention is not limited to the following examples.

The present invention is provided with 10-methoxycamptothecin derivatives having the general formula (1), wherein R is selected from hydrogen, $C_{1-6}$ alkyl, $C_{1-6}$ haloalkyl, aryl-substituted $C_{1-6}$ alkyl, phosphate-substituted $C_{1-6}$ alkyl, amino-substituted $C_{1-6}$ alkyl, carboxyl-substituted $C_{1-6}$ alkyl, hydroxyl-substituted $C_{1-6}$ alkyl, and amide-substituted $C_{1-6}$ alkyl; and $R_1$ is selected from hydrogen and t-butoxycarbonyl-amino.

In formula (1), if $R_1$ is hydrogen, R is selected from:

In formula (1), if $R_1$ is t-butoxycarbonyl-amino, R is selected from:

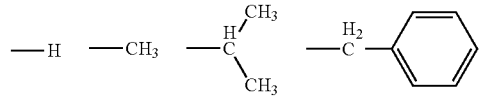

In particular, if R1 is t-butoxycarbonyl-amino, R is selected from:

The present invention provides a method for preparing the 10-methoxycamptothecin derivatives, which comprises reacting 10-methoxycamptothecin with N-t-butoxycarbonyl-amino acid or carboxylic acid by esterification under coupling agent and catalyst to obtain the 10-methoxycamptothecin derivatives of the formula (1).

The present invention also provides a drug composition containing the 10-methoxycamptothecin derivatives of the present invention and the pharmaceutically acceptable carriers.

Dosage form of the drug compositions can be selected from tablet, capsule, pill, injection, sustained-release preparation, controlled-release preparation, or various particulate drug delivery systems.

The invention also provides the use of the 10-methoxycamptothecin derivatives of the present invention in preparation of anti-tumor drugs.

Example 1

Preparation of 10-methoxycamptothecin-20-O-propionate 0.5 ml of propionic acid is added into 20 ml of dimethyl sulfoxide, and then 10-methoxycamptothecin 0.2 g, DCC 0.4 g and DMAP 0.06 g are added under stirring with reacting at room temperature for 24 hours, filtered and diluting the filtrates with 100 ml of distilled water to separate out white precipitates, and then filtering, washing, drying, and column chromatographic separation of the precipitates to obtain 165 mg of light yellow solid (yield 82%).

$^1$HNMR (400 MHz, DMSO-d6, ppm): δ0.92 (3H, t, H-19), 1.05 (3H, t, $CH_3$), 2.00 (2H, m, H-19), 2.53 (1H, t, $CH_2$), 3.94

(3H, s, OCH₃), 5.25 (2H, s, H-5), 5.48 (2H, s, H-17), 7.13 (1H, s, H-14), 7.48 (1H, d, H-11), 7.51 (1H, s, H-9), 8.05 (1H, d, H-12), 8.53 (1H, s, H-7).

ESIMS m/z: 433.3 (M+H)$^+$.

Example 2

Preparation of 10-methoxycamptothecin-20-O—(N'-t-butoxycarbonyl)-glycine ester 0.52 g of (N'-t-butoxycarbonyl)-glycine is dissolved in 20 ml of dimethyl sulfoxide, and then 10-methoxycamptothecin 0.2 g, CDI 0.4 g and DMAP 0.06 g are added under stirring with reacting at room temperature for 24 hours, filtered and diluting the filtrates with 100 ml of distilled water to separate out white precipitates, and then filtering, washing, drying, and column chromatographic separation of the precipitates to obtain 156 mg of light yellow solid (yield 78%).

$^1$HNMR (400 MHz, DMSO-d6, ppm): δ0.94 (3H, t, H-18), 1.32 (9H, s, t-boc), 2.13 (2H, m, H-19), 3.81 (1H, dd, C—H), 3.90 (3H, s, OCH₃), 3.98 (1H, dd, C—H), 5.17 (2H, s, H-5), 5.48 (2H, s, H-17), 7.13 (1H, s, H-14), 7.43 (1H, d, H-11), 7.44 (1H, t, N—H), 7.47 (1H, d, H-9), 7.97 (1H, d, H-12), 8.44 (1H, s, H-7). ESIMS: m/z 533.3 (M+H)$^+$.

Example 3

Preparation of 10-methoxycamptothecin-20-O—(N'-t-butoxycarbonyl)-L-alanine ester 0.56 g of (N'-t-butoxycarbonyl)-L-alanine is dissolved in 20 ml of N,N-dimethyl formamide, and then 10-methoxy-camptothecin 0.2 g, DCC 0.5 g and 0.5 ml of pyridine are added under stirring with reacting at room temperature for 24 hours, filtered and diluting the filtrates with 100 ml of distilled water to separate out white precipitates, and then filtering, washing, drying, and column chromatographic separation of the precipitates to obtain 147 mg of light yellow solid (yield 73%).

$^1$HNMR (400 MHz, DMSO-d6, ppm) 60.96 (3H, t, H-18), 1.33 (3H, t, CH₃), 1.44 (9H, s, t-boc), 2.09 (2H, m, H-19), 3.90 (3H, s, OCH₃), 4.09 (1H, t, C—H), 5.17 (2H, q, H-5), 5.48 (2H, s, H-17), 7.18 (1H, s, H-14), 7.39 (1H, d, H-11), 7.46 (1H, d, N—H), 7.61 (1H, d, H-9), 7.90 (1H, d, H-12), 8.42 (1H, s, H-7). ESIMS: m/z 548.4 (M+H)$^+$.

Example 4

Preparation of 10-methoxycamptothecin-20-O—(N'-t-butoxycarbonyl)-L-phenylalanine ester 0.79 g of (N'-t-butoxycarbonyl)-L-phenylalanine is dissolved in 20 ml of N,N-dimethyl formamide, and then 0.2 g of 10-methoxycamptothecin, 045 g of EDC.HCl and 0.5 ml of pyridine are added under stirring with reacting at room temperature for 24 hours, filtered and diluting the filtrates with 100 ml of distilled water to separate out white precipitates, and then filtering, washing, drying, and column chromatographic separation of the precipitates to obtain 150 mg of light yellow solid (yield 75%).

$^1$HNMR (400 MHz, DMSO-d6, ppm): δ0.95 (3H, t, H-18), 1.47 (9H, s, t-boc), 2.14 (2H, m, H-19), 2.98 (1H, m, C—H), 3.09 (1H, m, C—H), 3.92 (3H, s, OCH₃), 5.22 (2H, s, H-5), 5.50 (2H, s, H-17), 7.16 (1H, s, H-14), 7.27 (5H, m, C₅H₅), 7.47 (2H, m, H-11, N—H), 7.87 (1H, d, H-9), 8.16 (1H, d, H-12), 8.63 (1H, s, H-7).

ESIMS: m/z 624.4 (M+H)$^+$.

Example 5

Preparation of 10-methoxycamptothecin-20-O—(N'-t-butoxycarbonyl)-L-valine ester 0.59 g of (N'-t-butoxycarbonyl)-L-valine is dissolved in 20 ml of N,N-dimethyl formamide, and then 0.2 g of 10-methoxycamptothecin, 0.45 g of EDC.HCl and 0.06 g of DMAP are added under stirring with reacting at room temperature for 24 hours, filtered and diluting the filtrates with 100 ml of distilled water to separate out white precipitates, and then filtering, washing, drying, and column chromatographic separation of the precipitates to obtain 144 mg of light yellow solid (yield 72%).

$^1$HNMR (400 MHz, DMSO-d6, ppm) δ0.97 (9H, t, J=7.2 Hz, CH₃), 1.56 (9H, s, t-boc), 2.15 (3H, m, H-19, C—H), 3.98 (4H, s, OCH₃, C—H), 5.22 (2H, s, H-5), 5.48 (2H, s, H-17), 7.19 (1H, s, H-14), 7.47 (3H, m, H-11, H-9, N—H), 7.93 (1H, d, H-12), 8.42 (1H, s, H-7).

ESIMS: m/z 576.4 (M+H)$^+$.

The invention claimed is:

1. A 10-methoxycamptothecin derivative having a general formula (1),

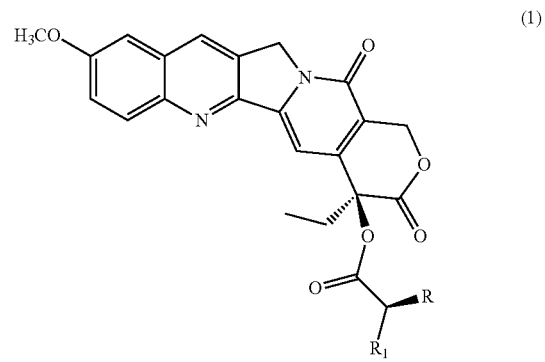

wherein R is selected from hydrogen, $C_{1-6}$ haloalkyl, aryl-substituted $C_{1-6}$ alkyl, phosphate-substituted $C_{1-6}$ alkyl, amino-substituted $C_{1-6}$ alkyl, carboxyl-substituted $C_{1-6}$ alkyl, hydroxyl-substituted $C_{1-6}$ alkyl, and amide-substituted $C_{1-6}$ alkyl; and $R_1$ is selected from hydrogen and t-butoxycarbonyl-amino; and wherein R and $R_1$ are different.

2. The 10-methoxycamptothecin derivative according to claim 1, wherein R is selected from hydrogen and aryl-substituted $C_{1-6}$ alkyl; and $R_1$ is selected from hydrogen and t-butoxycarbonyl-amino.

3. A drug composition containing the 10-methoxycamptothecin derivative according to claim 1 and pharmaceutically acceptable carriers.

4. The drug composition according to claim 3, wherein the dosage form of the drug composition is selected from tablet, capsule, pill, injection, sustained-release preparation, controlled-release preparation, or various particulate drug delivery systems.

5. The 10-methoxycamptothecin derivative according to claim 2, wherein $R_1$ is hydrogen.

6. The 10-methoxycamptothecin derivative according to claim 2, wherein if $R_1$ is t-butoxycarbonyl-amino, R is selected from:

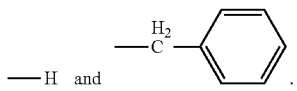 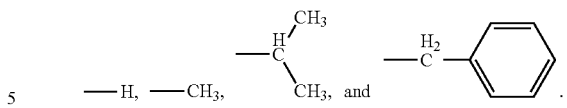

7. The 10-methoxycamptothecin derivative according to claim 2, wherein $R_1$ is t-butoxycarbonyl-amino.

8. A drug composition containing the 10-methoxycamptothecin derivative according to claim 2 and pharmaceutically acceptable carriers.

9. The drug composition according to claim 8, wherein the dosage form of the drug composition is selected from tablet, capsule, pill, injection, sustained-release preparation, controlled-release preparation, or various particulate drug delivery systems.

10. A 10-methoxycamptothecin derivative having a general formula (1),

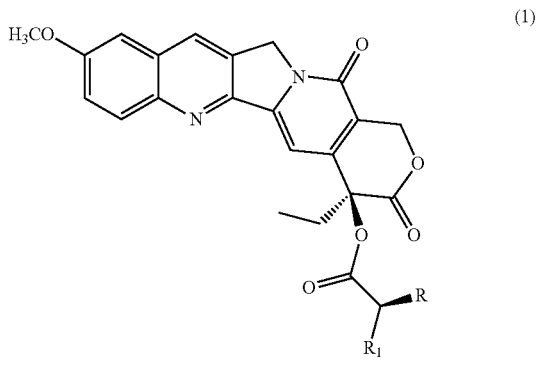

wherein R is selected from the group consisting of hydrogen, $C_{1-6}$ alkyl, $C_{1-6}$ haloalkyl, aryl-substituted $C_{1-6}$ alkyl, phosphate-substituted $C_{1-6}$ alkyl, amino-substituted $C_{1-6}$ alkyl, carboxyl-substituted $C_{1-6}$ alkyl, hydroxyl-substituted $C_{1-6}$ alkyl, and amide-substituted $C_{1-6}$ alkyl; and $R_1$ is t-butoxycarbonyl-amino.

11. The 10-methoxycamptothecin derivative according to claim 10, wherein if $R_1$ is t-butoxycarbonyl-amino, R is selected from:

12. The 10-methoxycamptothecin derivative according to claim 10, wherein if $R_1$ is t-butoxycarbonyl-amino, R is:
—$CH_3$.

13. A 10-methoxycamptothecin derivative having a general formula (1),

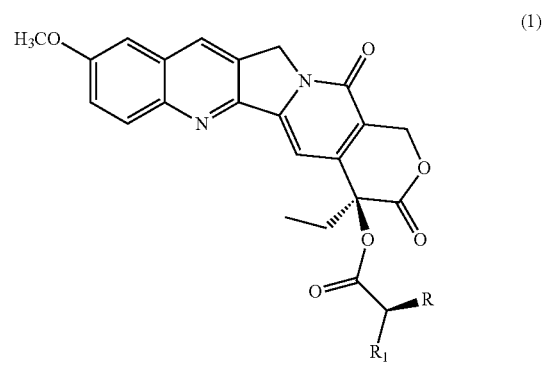

wherein R is selected from the group consisting of

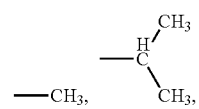

$C_{1-6}$ haloalkyl, aryl-substituted $C_{1-6}$ alkyl, phosphate-substituted $C_{1-6}$ alkyl, amino-substituted $C_{1-6}$ alkyl, carboxyl-substituted $C_{1-6}$ alkyl, hydroxyl-substituted $C_{1-6}$ alkyl, and amide-substituted $C_{1-6}$ alkyl; and $R_1$ is hydrogen.

14. The 10-methoxycamptothecin derivative according to claim 13, wherein if $R_1$ is hydrogen, R is:
—$CH_3$.

* * * * *